United States Patent [19]

Theriault

[11] 3,948,884
[45] Apr. 6, 1976

[54] MYCAROSYL MACROLIDE ANTIBIOTICS

[75] Inventor: Robert John Theriault, Kenosha, Wis.

[73] Assignee: Abbott Laboratories, North Chicago, Ill.

[22] Filed: Sept. 6, 1973

[21] Appl. No.: 394,905

Related U.S. Application Data

[62] Division of Ser. No. 246,095, April 17, 1972, Pat. No. 3,784,447.

[52] U.S. Cl. .............................. 260/210 AB; 424/180
[51] Int. Cl.² ............................................. C07H 17/00
[58] Field of Search ............... 260/210 AB; 424/180; 195/80

[56] References Cited
OTHER PUBLICATIONS

*Macrolide Antibiotics*, Encyclopedia of Chem. Technology, Vol. 12, 1967, Wiley and Sons, pp. 632–661.

Omura et al., Studies on Chem. Structure . . . Their Related Macrolide Antibiotics, Progress in Antimicrobial and Anticancer Chemotherapy, Vol. 12, 1970, pp. 1043–1049.

Huber et al., Arzneimittel Forschung, Vol. 12, pp. 1191–1195, 1962.

Omura et al., "*Among Leucomycins . . . Derivatives*" *J. of Antibiotics*, Vol. 21, 1968, pp. 532–538.

*Primary Examiner*—Johnnie R. Brown
*Assistant Examiner*—Cary Owens
*Attorney, Agent, or Firm*—Robert L. Niblack; James L. Bailey; Vincent A. Mallare

[57] ABSTRACT

Covers the desisovaleryl derivative of niddamycin. Also covers a method of performing the microbial conversion of niddamycin, magnamycin A, magnamycin B, leucomycin $A_1$ and leucomycin $A_3$ to the corresponding desisovaleryl derivatives. These desisovaleryl derivatives are useful as antibiotics.

1 Claim, No Drawings

MYCAROSYL MACROLIDE ANTIBIOTICS

This is a division of application Ser. No. 246,095 filed Apr. 17, 1972, now U.S. Pat. No. 3,784,447 issued Jan. 8, 1974.

BRIEF DESCRIPTION OF THE DISCLOSURE

This invention relates to a new and useful derivative of niddamycin and to a method of preparing via microbial conversion said niddamycin derivatives as well as derivatives of magnamycins A an B and leucomycins $A_1$ and $A_3$. More particularly, this invention pertains to a niddamycin antibiotic composition having the following structural formula:

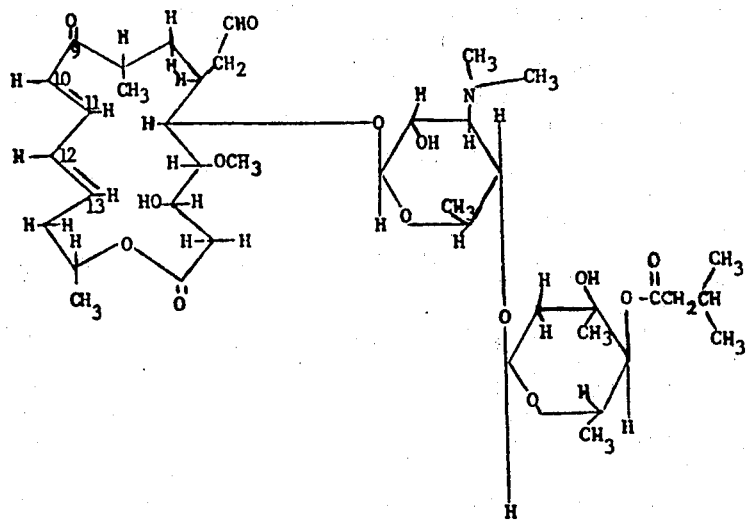

The invention is also particularly concerned with a method of preparing the following antibiotic compositions falling within the structural formula:

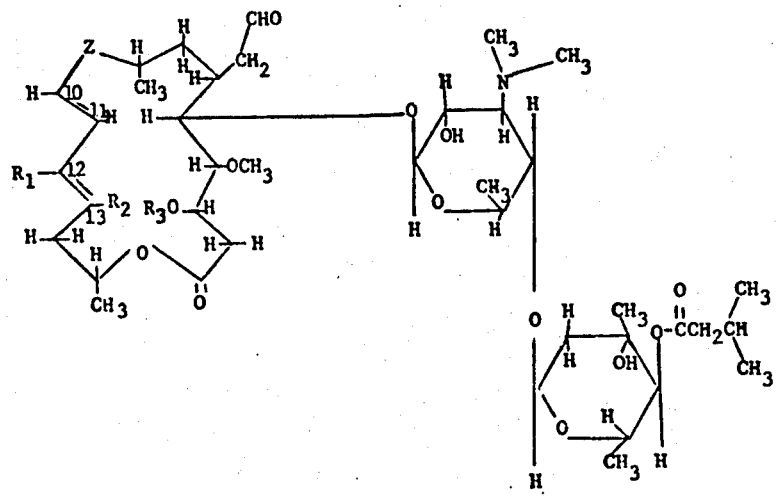

where Z is

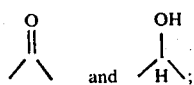

$R_1$ and $R_2$ when taken separately are each hydrogen and when taken together epoxy; and $R_3$ represents hydrogen and acetyl.

These compounds are prepared by the microbial conversion of niddamycin, magnamycin A, magnamycin B, leucomycin $A_1$ and leucomycin $A_3$ to the corresponding desisovaleryl compounds falling within the structural formula just set out. The microbial conversion is carried out by inoculating one of the cultures listed below in a fermentation medium for sufficient time to allow incubation and growth, adding the niddamycin, leucomycin or magnamycin substrate to the fermentation medium, allowing sufficient time in order to permit the conversion to the corresponding desisovaleryl derivative to take place, and isolating said desisovaleryl derivative.

DETAILED DESCRIPTION OF THE INVENTION

In more detail, the desisovaleryl derivatives of niddamycin, magnamycins A and B and leucomycins $A_1$ and $A_3$ are prepared by microbial transformation by resort to the following micro-organisms:

Cunninghamella elegans ATCC9245
Cunninghamella elegans QM6784
Cunninghamella echinulata QM6782
Cunninghamella echinulata NRRL11498
Cunninghamella verticillata ATCC8983
Helicostylum puriforme ATCC8992
Mortierella ramanniana ATCC11715
Monilia fructicola NRRL3945
Penicillium chrysogenum Wisconsin Q-176
Penicillium lilacinum NRRL895
Penicillium janthinellum NRRL2016

*Penicillium dalae* NRRL2025
Penicillium species A-85 NRRL3282
*Sporotrichum sulfurescens* ATCC7159
*Trichoderma viride* NRRL1762
*Pestalotiopsis royenae* ATCC11816
*Streptomyces (cinnamomeus)* NRRLB1285
*Streptomyces factor* NRRL3113
Streptomyces species ACT-27 NRRL3948
*Lentodium squamosum* G-17 NRRL3943
Dermoloma species F-27 NRRL3942

The notation "ATTC" indicates a culture of the organism has been placed on deposit with the American Type Culture Collection, Rockville, Maryland; the notation "NRRL" indicates the culture of the organism has been placed on deposit with the Northern Utilization Research and Development Division, Department of Agriculture, Peoria, Ill.; and the notation "QM" similarly indicates the depository is the Quartermaster Research and Development Center, United States Army, Natick, Massachusetts.

Suitable growth media for the micro-organisms comprises assimilable sources of carbon, nitrogen, defoamers and buffers. Examples of such nitrogen sources include soy bean flour, yeast extract, corn meal, oatmeal, meal extracts, distillers' solubles, protein hydrolysates, peptones, amino acids, urea, nitrates, and amonium compounds. Carbohydrates, especially monosaccharides can be used as a carbon source and include glucose, frutose, sucrose, maltose, lactose, molasses, dextrines, and starches.

The fermentation media used in this process are designated as A, B and C and contain the following ingredients:

| Fermentation Media A | g/liter |
| --- | --- |
| Glucose monohydrate (added post sterilization) | 50.0 |
| Soybean flour | 5.0 |
| Yeast extract | 5.0 |
| NaCl | 1.0 |
| $KH_2PO_4$ | 4.1 |
| $K_2HPO_4$ | 0.8 |

Adjust pH to 6.0 and add deionized water to 1.0 liter

| Fermentation Media B | g/liter |
| --- | --- |
| Glucose monohydrate (added post sterilization) | 50.0 |
| Soybean flour | 5.0 |
| Yeast extract | 5.0 |
| NaCl | 1.0 |
| Malt extract | 20.0 |
| $KH_2PO_4$ | 4.1 |
| $K_2HPO_4$ | 0.8 |

Adjust pH to 6.0 and add deionized water to 1.0 liter.

| Fermentation Media C | g/liter |
| --- | --- |
| Glucose monohydrate (added post sterilization) | 50.0 |
| Soybean grits | 5.0 |
| Yeast extract | 2.5 |
| NaCl | 1.0 |
| $K_2HPO_4$ | 2.0 |
| $KH_2PO_4$ | 1.0 |

Adjust pH to 7.0 and add deionized water to 1.0 liter

The following examples illustrate the process of the invention.

EXAMPLE 1

Cultures belonging to the genera Cunninghamella, Helicostylum, Mortierella, Monilia, Penicillum, Sporotrichum, Trichoderma, and Pestalotiopsis, were preferably inoculated from agar slant cultures into sterile cotton plugged flasks containing an increment of the sterile fermentation medium A. Those cultures belonging to the genus Streptomyces were preferably inoculated from agar slant cultures into similar sterile flasks containing an increment of sterile fermentation medium C. Cultures belonging to the genera Lentodium and Dermoloma were preferably inoculated from agar slant cultures into similar flasks containing an increment of sterile medium B. After inoculation, the flasks were incubated at a temperature of from 24°–28°C. and preferably at approximately 28°C. on a rotary shaker. After 48 hours to 96 hours incubation, niddamycin was added to each flask at a level of 0.05% (50 mg/100 ml. medium). The flasks were again incubated on the shaker. The flasks were sampled at various ages during the fermentation and analyzed by thin-layer chromatography in order to follow the rate of conversion.

The chromatographic analysis was carried out as follows:

Ten milliliters of whole culture were adjusted to pH about 8.5 with $NH_4OH$. 10 ml. of acetone was added with shaking. The whole culture:acetone samples were then extracted with 20 ml. of ethyl acetate twice. The ethyl acetate extracts were evaporated under vacuum and the residues obtained were reconstituted in 2.5 ml. of methanol. The methanol solutions were spotted (200 microliters on 20×20 cm. glass plates coated with Merck-Darmstadt silica gel plates. The thin-layer plates were developed in one of the following solvent systems:

I $CH_2Cl_2$: 95% aqueous $CH_3OH:H_2O$ (85:15:1)
II $CH_2Cl_2$: 95% aqueous $CH_3OH:NH_4OH$ (90:10:1)

After 30 to 45 minutes developing time, the thin-layer plates were removed and dried. Ultra-violet absorbing compounds were photographed with ultra-violet light (254 nm.) Niddamycin and related microbial conversion products were then revealed by spraying the plates with anisaldehyde reagent.

Niddamycin moved to an $R_f$ of 0.65 to 0.70 in solvent system II and 0.77 to 0.82 in solvent system I. In solvent system II the product desisovalerylniddamycin had an $R_f$ value of 0.3 and 0.37. In solvent system I desisovalerylniddamycin had an $R_f$ value of from 0.57 to 0.65. All of the previously cited cultures formed varying amounts of the apparent desisovalerylniddamycin by thin-layer chromatography, $R_f$. This product absorbed short wave ultra-violet light at 254 nm indicating probably no change in the conjugated system. After spraying the plates with anisaldehyde reagent (95% $C_2H_5OH$:Conc $H_2SO_4$: anisaldehyde (9:1:1) and heating to 100°C. for 5–10 minutes in an oven, niddamycin was revealed as a black spot. The microbial conversion product was characterized by a rather unique purple-red color. Like niddamycin, the new antibiotic inhibited *B. subtilis* and *S. aureus* on bioautograph plates.

EXAMPLE 2

Twenty cotton plugged sterile 500 ml. Erlenmeyer flasks each containing 100 ml. of sterile medium A were each inoculated with one-half of an agar slant culture of *Cunninghamella elegans* QM6784. Twenty similar flasks each containing 100 ml. of sterile medium C were inoculated with one-half of an agar slant culture of Streptomyces species AcT-27 NRRL3948. All flasks were incubated on a Gump rotary shaker at 28°C. After 48 hours incubation, 0.05% niddamycin (50 mg/100 ml. medium) was added to each flask. The flasks were returned to the shaker and sampled at various ages, during the fermentation for solvent extraction and thin-layer chromatography analysis as previously described. Although harvest can take place anywhere from 144 hours to 312 hours, in this example flasks were harvested at 216 hours. The contents of the 20 flasks of each culture were pooled separately. The pooled harvest whole culture was adjusted to pH about 8.5 with $NH_4OH$, adding a substantially equivalent volume of acetone with mixing. The whole culture:acetone beer of each culture was then extracted with 2 volumes of ethyl acetate twice. The ethyl acetate extracts were dried under vacuum. The residue obtained from each culture extract was reconstituted in a small volume of methylene chloride and chromatographed in a silica gel column. The major microbial conversion product which again appeared to be the same for both cultures, was separated from residual niddamycin and other impurities on the column by or with increased levels of methanol in methylene chloride. Final purification of the major microbial conversion product of each culture was achieved by preparative thin-layer chromatography. The purest column fractions were concentrated and streaked on a series of silica gel $GF^{254}$ thin-layer chromatography plates which were developed in the $CH_2CL_2$:95% aqueous $CH_3OH$:$H_2O$ (85:15:1) solvent system. The major conversion product was located with 254 nm light, and eluted in methanol. The product was dried, redissolved in ethyl acetate, filtered and finally dried. The isolated purified product from both *Cunninghamella elegans* QM6784 and Streptomyces species Act-27 NRRL3948 was submitted for mass spectra analysis. Both products showed a loss of the isovaleric acid from the molecule indicating a tentative structure of desisovalerylniddamycin. The product from Streptomyces species Act-27 NRRL3948 exhibited a 100 MHz nmr spectrum which was consistent with a structure of desisovalerylniddamycin.

EXAMPLE 3

Two hundred sterile cotton plugged 500 ml. Erlenmeyer flasks each containing 100 ml. of sterile medium C were each inoculated with 1/2 of an agar slant culture of Streptomyces species Act-27 NRRL3948. The flasks were then incubated on a Gump rotary shaker (about 250 tpm) at 28°C. for 48 to 72 hours. At that time, the culture or mycelia from each flasks was pooled in sterile 5 gallon glass carboys. The pooled mycelia was allowed to settle and the supernate fermentation liquor was decanted and discarded. The pooled mycelia was then washed three times and resuspended at the original volume with sterile 0.01M pH 7.0, $K_2HPO_4$, $KH_2PO_4$ buffer. The washed mycelia was then redispensed into the original 500 ml. cotton plugged Erlenmeyer flasks and at the same volume of 100 ml. 0.05% niddamycin was added in powdered form (50 mg/100 ml. washed mycelia) to each flask. The flasks were returned to the shaker for anywhere from 8 hours to 72 hours during which time good yields of desisovalerylniddamycin were formed. Forty-eight hours was usually optimal for complete utilization of the substrate and good yields of the desired product.

The washed mycelia, phosphate buffer suspension from each flask was again pooled. Since none of the desisovalerylniddamycin was present in the mycelia, the pooled mycelia buffer suspension was filtered through heavy frame press filter paper, and the mycelia was discarded. One half volume of methanol was added to the filtrate to further precipitate finely suspended mycelium which was again removed by filtration. The methanolphosphate buffer filtrate containing virtually all of the desisovalerylniddamycin was then concentrated under vacuum from approximately 18 to 19 liters down to 1 to 2 liters at a temperature of 30°C. The concentrated filtrate was then adjusted to pH 7.5 with $NH_4OH$ and one volume of methanol was added. This suspension was then extracted three times with methylene chloride. The methylene chloride extracts containing all of the desired product were evaporated to dryness under vacuum yielding approximately 6 gm. of impure desisovalerylniddamycin plus other impurities. This material was chromatographed on a 6 cm. diameter glass column packed with Merck Darmstadt silica gel $GF^{254}$ and developed with a solvent system consisting of ethyl acetate: methanol: $H_2O$ (90:10:1). Desisovalerylniddamycin fractions were eluted, pooled and dried. These fractions were further purified as follows by chromatography on a partition column:

A 5.4 cm. diameter glass column was partially filled with the mobile or upper phase of the following solvent system: n-heptane:benzene:acetone:isopropyl alcohol; 0.01 1M phosphate buffer pH 7 (25:10:15:10:25). The glass column containing the mobile phase was then packed with silica gel $GF^{254}$ previously moistened with the immobile or lower phase of the solvent system (0.9 ml/gm of silica gel) to a height of about 52 cm. Desisovalerylniddamycin dried fractions were dissolved in a small volume of the mobile phase, added to the column, and developed with the mobile phase. Column fractions were monitored by thin-layer chromatography. Desisovalerylniddamycin crystallized directly in the column fraction tubes. The mass spectrum and nmr spectrum of the crystalline product was again consistent with a structure of desisovalerylniddamycin.

EXAMPLE 4

Microbial Conversion of Niddamycin to Desisovalerylniddamycin in 30 Liter Fermentors

| | |
|---|---|
| Fermentor medium: | Medium C |
| Fermentor charge volume: | 12 liters |
| Antifoam: | 0.005% Hodag F-1 |
| Sterilization time: | 1.0 hr. at 121°C. and 15–16 lbs. pressure |
| Inoculum: | 5.0% vegetative inoculum from 72 hours 28°C., Medium C shaken flasks of Streptomyces species Act-27 NRRL3948 |
| Fermentor Incubation Temperature | 28°C. |
| Fermentor agitation rate | 410 rpm |
| Fermentor air rate | 0.6 liter/liter/min. |

Two fermentors (30 Liter) was inoculated and incubated as described above for 48 hours. At that time, 0.05% niddamycin was added to powdered form to each fermentor. Incubation was continued for an additional 24 hours to 72 hours. Samples were taken after substrate addition for thin-layer chromatography analysis as previously described. Optimal conversion of niddamycin to desisovalerylniddamycin occurred from 24 hours to 120 hours after inoculation. The harvested fermentation beer was pooled, adjusted to pH 7.5 with NH$_4$OH and one volume of methanol was added. The methanol:harvest culture suspension was then filtered through a frame press and the filtrate was concentrated to about 1.0 liter with a vertical evaporator under vacuum at about 30°C. The concentrated filtered beer was again diluted with one volume of methanol, adjusted to 7.5 with NH$_4$OH and finally extracted with 3 volumes of methylene chloride three times. The methylene chloride extracts were combined and evaporated to dryness under vacuum. The residue obtained, containing all of the impure desisovalerylniddamycin, was dissolved in a small volume of methylene chlordie:methanol (95:5) and then chromatographed on a 6.0 cm. diameter glass column slurry packed with silica gel GF$^{254}$ in methylene chloride:methanol (95:5). Desisovalerylniddamycin fractions were eluted, pooled, dried under vacuum and rechromatographed on the previously described partition chromatography column. The column was developed with the mobile phase of the solvent system and fractions of reasonably pure desisovalerylniddamycin were collected. Desisovalerylniddamycin was allowed to crystallize directly in the column fractions or the fractions were pooled, dried under vacuum as pure amorphous desisovalerylniddamycin.

| Desisovalerylniddamycin Physical Properties | |
|---|---|
| Melting Point | 132–134°C |
| Mass Spectrum | Molecular ion (M)+= 699.3829 (Calculated for $C_{35}H_{57}NO_{13}$=699.3829) |
| Optical Rotation | $[\alpha]_D^{23.5°}$ –54° (C 1.00 absolute methanol) |

The 100 MHz nmr spectrum was also consistent with a structure of desisovalerylniddamycin.

The same preparative techniques outlined above can be used to produce the desisovaleryl derivatives of magnamycins A and B and leucomycins A$_1$ and A$_3$.

The desisovalerylniddamycin compound was then tested for its anti-microbial spectrum. The in vitro activity of the desisovalerylniddamycin compound was tested as follows:

The microbial conversion product of niddamycin (desisovalerylniddamycin) was submitted for antibacterial testing against fifteen organisms. The standard agar two-fold dilution method was used in Brain Heart Infusion Agar, 10 ml./ plate. Inoculum was a loopful of a 1:100 dilution of a 24 hour broth culture with the exception of the Staphylococci which used as undiluted culture. Incubation was at 37°C for 24 hours. Niddamycin was used as the comparison control. Results are as follows with M.I.C. values (minimum inhibiting concentration) being given in mcg/ml figures.

RESULTS:

| | Niddamycin | Desisovalerylniddamycin |
|---|---|---|
| Staph aureus 9144 | 0.78 | 1.56 |
| Staph aureus Smith | 0.78 | 1.56 |
| Staph aureus Smith ER | 500.0 | >1,000.0 |
| Staph aureus Quinones | 1.56 | 6.2 |
| Staph aureus Wise 155 | 1.56 | 6.2 |
| Strep faecalis 10541 | 1.56 | 3.1 |
| E. Coli Juhl | 500.0 | 1,000.0 |
| Klebsiella pneumoniae 10031 | 25.0 | 50.0 |
| Proteus vulgaris JJ | >1,000.0 | >1,000.0 |
| Proteus mirabilis Fin No. 9 | 1,000.0 | >1,000.0 |
| Salmonella typhimirium ED No. 9 | 500.0 | 500.0 |
| Shigella sonnei 9290 | 250.0 | 500.0 |
| Pseudomonas aeruginosa BMH No. 10 | >1,000.0 | >1,000.0 |
| Strep pyogenes Roper | >1,000.0 | >1,000.0 |
| Pasturella multocida 10544 | 12.5 | 50.0 |

It should be understood that in the above structures when R$_1$ and R$_2$ are taken together to represent epoxy, no double bond then exists between carbon numbers twelve and thirteen.

I claim:
1. The desisovaleryl derivative of niddamycin.

* * * * *